US010538801B2

(12) United States Patent
Yamaguchi et al.

(10) Patent No.: US 10,538,801 B2
(45) **Date of Patent: *Jan. 21, 2020**

(54) METHOD FOR DETERMINING WHETHER OR NOT TEST SAMPLE CONTAINS EXSEROHILUM PHYTOPATHOGENIC FUNGUS

(71) Applicant: Panasonic Intellectual Property Management Co., Ltd., Osaka (JP)

(72) Inventors: Kaori Yamaguchi, Fukui (JP); Yoshitsugu Uriu, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 34 days.

This patent is subject to a terminal disclaimer.

(21) Appl. No.: 15/844,629

(22) Filed: Dec. 18, 2017

(65) Prior Publication Data

US 2018/0208961 A1 Jul. 26, 2018

(30) Foreign Application Priority Data

Jan. 25, 2017 (JP) ................................ 2017-010911

(51) Int. Cl.
*C12Q 1/06* (2006.01)

(52) U.S. Cl.
CPC .......... *C12Q 1/06* (2013.01); *G01N 2333/37* (2013.01)

(58) Field of Classification Search
CPC ....................................................... C12Q 1/06
See application file for complete search history.

(56) References Cited

U.S. PATENT DOCUMENTS

2016/0355863 A1 12/2016 Uriu
2016/0355864 A1 12/2016 Uriu

FOREIGN PATENT DOCUMENTS

JP 2005-287337 10/2005

OTHER PUBLICATIONS

Cao et al. Ind. Eng. Chem. Res., 2006, 45:4193-4199.*
Candau et al. Applied and Environmental Microbiology, 1991, 57(11):3378-3382.*
Paul F. Morris et al., "Chemotropic and Contact Responses of Phytophthora sojae Hyphae to Soybean Isoflavonoids and Artificial Substrates", Plant Physiol. (1998) 117:1171-1178, Aug. 1, 1998.
Roberto Luis De Rossi et al., "Semi-selective culture medium for Exserohilum turcicum isolation from corn seeds", Summa Phytopathol., Botucatu, vol. 40, No. 2, pp. 163-167, Jun. 9, 2014.

* cited by examiner

*Primary Examiner* — Bin Shen
(74) *Attorney, Agent, or Firm* — McDermott Will & Emery LLP

(57) ABSTRACT

The present invention provides a method for determining whether or not a test sample contains an *Exserohilum* phytopathogenic fungus. The method comprises: (a) putting the test sample on a front surface of a cellulose film having no through hole; (b) leaving the test sample at rest for a predetermined time; (c) observing a back surface of the cellulose film; and (d) determining that the test sample contains the *Exserohilum* phytopathogenic fungus, if a fungus which has penetrated the cellulose film is found on the back surface of the cellulose film in the step (c). The method further comprises a step of supplying a culture medium to the test sample before the step (b). The culture medium is a lactose casein hydrolysate agar medium containing carbendazim, captan, streptomycin sulfate, and neomycin sulfate. Alternatively, in the step (b), the test sample is left at rest while the back surface of the cellulose film is in contact with the culture medium.

22 Claims, 9 Drawing Sheets

--- Prior Art ---

METHOD FOR DETERMINING WHETHER OR NOT TEST SAMPLE CONTAINS EXSEROHILUM PHYTOPATHOGENIC FUNGUS

This application claims the benefit of foreign priority of Japanese patent application 2017-010911 filed on Jan. 25, 2017, the content of which is incorporated herein by reference.

BACKGROUND

1. Technical Field

The present invention relates to a method for determining whether or not a test sample contains an *Exserohilum* phytopathogenic fungus.

2. Description of the Related Art

PTL1 discloses a method for counting the number of mold cells in a specimen by the culture for a short time and capable of accurately counting the cell number. FIG. 12 shows a cross-sectional view of a microporous membrane supporting material used for the method disclosed therein. According to this method, the extended multiple pseudomycelia of a mold cell 13 cultured by a liquid culture or a mold cell 13 cultured on a microporous membrane 1 of a microporous membrane supporting material 4 are photographed and the shape, area and luminous intensity are recognized and analyzed by an image analytic means 10. The number of the mold cells 13 can be counted by the culture for a short time. The microporous membrane 1 is interposed between a pressing ring 2 and a base 3.

NPL 1 discloses that pseudohyphae of *Phytophthora sojae*, which is one of phytopathogenic oomycetes, penetrates the PET membrane having 3-micrometer pores.

NPL2 discloses a semi-selective culture medium in which only an *Exserohilum* genus is grown.

CITATION LIST

Patent Literature

PTL1: Japanese Patent Application laid-open Publication No. 2005-287337A

Non-Patent Literature

NPL1: Paul F. Morris. et. al. "Chemotropic and Contact Responses of *Phytophthora sojae* Hyphae to Soybean Isoflavonoids and Artificial Substrates", Plant Physiol. (1998) 117: 1171-1178

NPL2: Roberto Luis De Rossi et. al. "Semi-selective culture medium for *Exserohilum turcicum* isolation from corn seeds", Summa Phytopathol., Botucatu, vol. 40, no. 2, p. 163-167, 2014

SUMMARY

An object of the present invention is to provide a method for determining whether or not a test sample contains an *Exserohilum* phytopathogenic fungus.

The present invention provides a method for determining whether or not a test sample contains an *Exserohilum* phytopathogenic fungus, the method comprising:

(a) putting the test sample on a front surface of a cellulose film having no through hole;

(b) leaving the test sample at rest for a predetermined time after the step (a);

(c) observing a back surface of the cellulose film after the step (b); and (d) determining that the test sample contains the *Exserohilum* phytopathogenic fungus, if a fungus which has penetrated the cellulose film is found on the back surface of the cellulose film in the step (c);

wherein the method further comprises a step of supplying a culture medium to the test sample before the step (b); and the culture medium is a lactose casein hydrolysate agar medium containing:

carbendazim, captan, streptomycin sulfate; and neomycin sulfate.

The present invention also provides a method for determining whether or not a test sample contains an *Exserohilum* phytopathogenic fungus, the method comprising:

(a) putting the test sample on a front surface of a cellulose film having no through hole;

(b) leaving the test sample at rest for a predetermined time after the step (a);

(c) observing a back surface of the cellulose film after the step (b); and (d) determining that the test sample contains the *Exserohilum* phytopathogenic fungus, if a fungus which has penetrated the cellulose film is found on the back surface of the cellulose film in the step (c);

wherein in the step (b), the test sample is left at rest while the back surface of the cellulose film is in contact with a culture medium; and the culture medium is a lactose casein hydrolysate agar medium containing:

carbendazim;

captan;

streptomycin sulfate; and neomycin sulfate.

The present invention provides a method for determining whether or not a test sample contains an *Exserohilum* phytopathogenic fungus.

DETAILED DESCRIPTION OF THE EMBODIMENT

The term "phytopathogenic" means to have pathogenicity to plants. The term "non-phytopathogenic" means not to have pathogenicity to plants. Even if a fungus has pathogenicity, however, if the fungus has no pathogenicity to plants, the fungus is non-phytopathogenic. In other words, if a fungus does not have adverse effects on plants, the fungus is non-phytopathogenic. The prefix "non-" included in the term "non-phytopathogenic" does not modify "phyto". The prefix "non-" modifies "pathogenic".

Hereinafter, the embodiment of the present invention will be described in more detail with reference to the drawings.

(Step (a))

In the step (a), a test sample is put on a front surface of a cellulose film having a thickness of not more than 14.5 micrometers. As one example, the cellulose film has a thickness of not less than 0.04 micrometers and not more than 14.5 micrometers. It would be difficult to form a cellulose film having a thickness of less than 0.04 micrometers. On the other hand, it takes too long a time for an *Exserohilum* phytopathogenic fungus to penetrate a cellulose film having a thickness of more than 14.5 micrometers. Therefore, the cellulose film having such a thickness is not impracticable.

Figure 1:
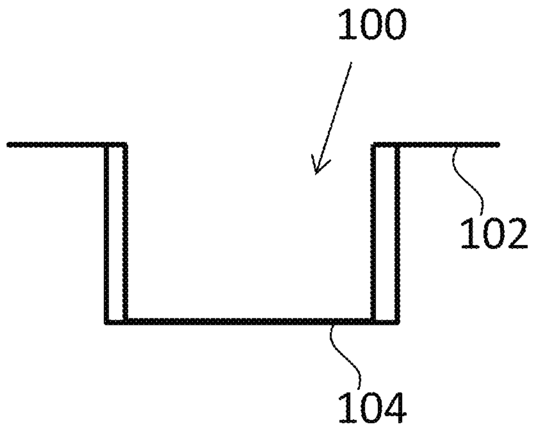
FIG. 1 shows a cross-sectional view of a first container.

In particular, as shown in FIG. 1, a container 100 is prepared. It is desirable that the container 100 comprises a flange 102 at the upper end thereof. The bottom surface of the container 100 is formed of a cellulose film 104. It is desirable that the cellulose film 104 is supported by a substrate (not shown in FIG. 1). This will be described later.

Figure 3:
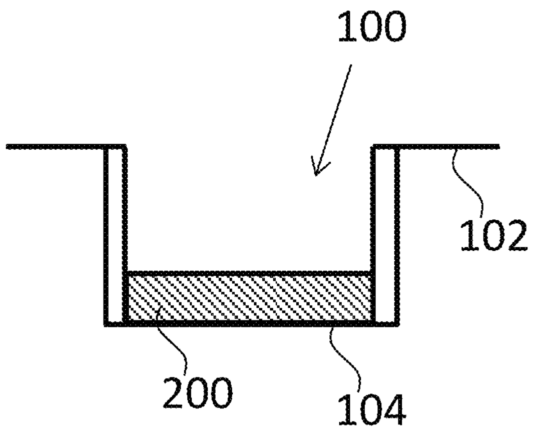
FIG. 3 shows a cross-sectional view of the first container to which a test sample has been supplied.
Figure 4:
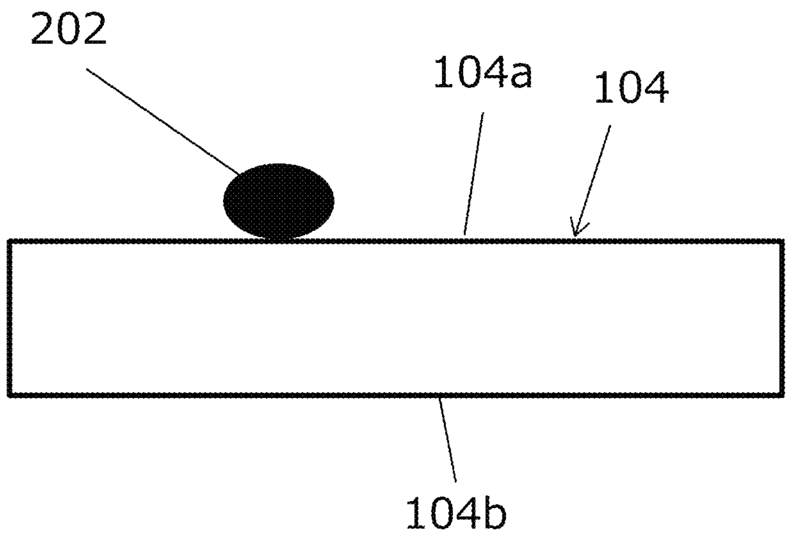
FIG. 4 shows a cross-sectional view of the cellulose film having a front surface on which a phytopathogenic fungus has been put.

As shown in FIG. 3, a test sample 200 is supplied to the inside of this container 100. In this way, the test sample 200 is put on a front surface 104*a* of the cellulose film 104. When the test sample 200 contains a phytopathogenic fungus 202, the phytopathogenic fungus 202 is put on the front surface 104*a* of the cellulose film 104, as shown in FIG. 4.

The test sample 200 is solid, liquid, or gaseous. It is desirable that the test sample 200 is solid or liquid. An example of the solid test sample 200 is soil or a crushed plant. Another example is an agricultural material such as vermiculite, rock wool or urethane. An example of the liquid test sample 200 is agricultural water, a solution used for hydroponic culture, a liquid used for washing a plant, a liquid extracted from a plant, a liquid used for washing an agricultural material, or a liquid used for washing clothing or shoes of a worker.

(Step (b))

In the step (b), the test sample 200 is left at rest for a certain incubation time after the step (a). As one example, the incubation time is 24 hours.

Figure 2:
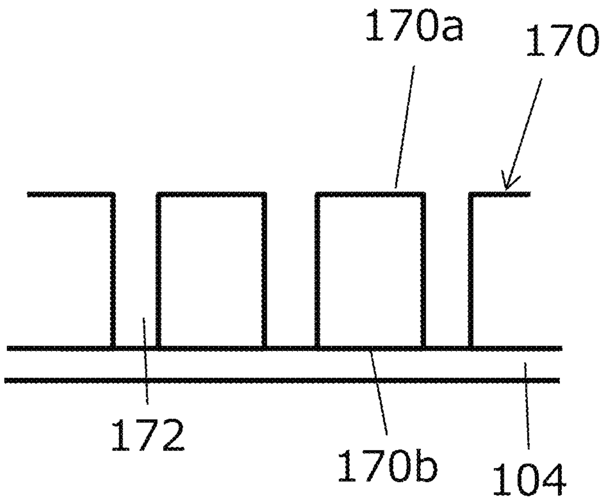
FIG. 2 shows a cross-sectional view of a cellulose film supported by a back surface of a substrate.

As shown in FIG. 2, the cellulose film 104 may comprise a substrate 170 comprising a through hole 172 on at least one of the front surface 104*a* and a back surface 104*b* thereof. In FIG. 2, the cellulose film 104 comprises the substrate 170 on the front surface thereof. In other words, in FIG. 2, the substrate 170 comprises the cellulose film 104 on a back surface 170*b* thereof. It is desirable that the through hole 172 has a diameter of more than 5 micrometers. More desirably, the through hole 172 has a diameter of not less than 8 micrometers. In case where the through hole 172 has a diameter of not more than 5 micrometers, the non-phytopathogenic fungus seldom reaches the inside of the through hole 172. As a result, the non-phytopathogenic fungus fails to be brought into contact with the front surface of the cellulose film 104. For more detail, see United States Patent Application Publications No. 2016/0355863 and No. 2016/0355864, both of which are incorporated herein by reference.

Needless to say, as long as the cellulose film 104 is stretched taut, the substrate 170 is not required. In other words, if it is difficult to stretch the cellulose film 104 taut, the substrate 170 for supporting the cellulose film 104 is used.

A reference number 170*a* indicates the front surface of the substrate 170. As shown in FIG. 2, it is desirable that the substrate 170 has a plurality of through holes 172. The thickness of the substrate 170 is not limited; however, as one example, it is desirable that the substrate 170 has a thickness of not less than 1 micrometer and not more than 500 micrometers. The cellulose film 104 is significantly thin. However, if the cellulose film 104 is arranged on the substrate 170, it is easy to handle the cellulose film 104. As shown in FIG. 2, note that the cellulose film 104 has no through hole.

In the present embodiment, a culture medium is supplied to the test sample 200. As disclosed in Roberto Luis De Rossi et. al., the culture medium is a lactose casein hydrolysate agar medium containing carbendazim, captan, streptomycin sulfate; and neomycin sulfate. By using the culture medium, only an *Exserohilum* phytopathogenic fungus penetrates the cellulose film 104 to selectively appear on the back surface of the cellulose film 104 in the step (d). In other words, phytopathogenic fungi other than an *Exserohilum* phytopathogenic fungus do not appear on the back surface of the cellulose film 104 in the step (d).

In particular, a culture medium is supplied to the inside of the container 100 containing the test sample 200. It is desirable that the culture medium is liquid. The culture medium is supplied in the step (b). Alternatively, the culture medium is supplied prior to the step (b). In other words, the culture medium is supplied in the step (a). The culture medium may be supplied to the inside of the container 100 prior to the step (a).

Figure 6:
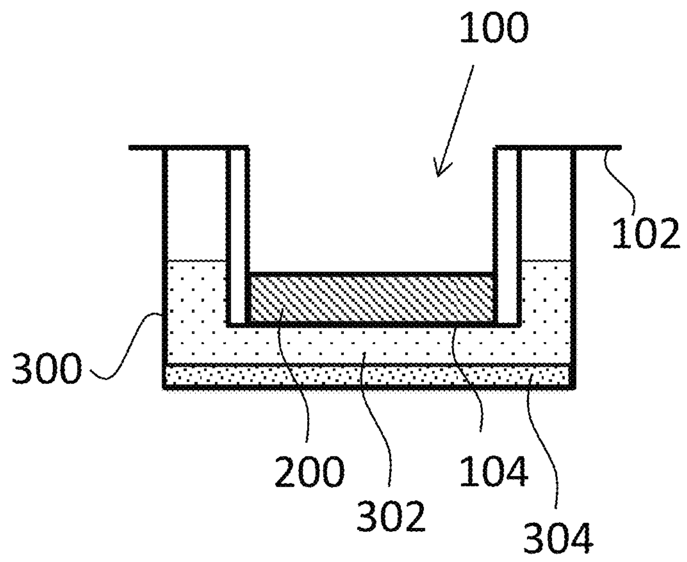
FIG. 6 shows a cross-sectional view of one example of a method for accelerating the incubation of the fungus.

FIG. 6 shows another embodiment of the supply of the culture medium. As shown in FIG. 6, it is desirable that the back surface 104*b* of the cellulose film 104 is in contact with a liquid culture medium 302. First, a second container 300 having the liquid culture medium 302 therein is prepared. Hereinafter, the container 100 is referred to as "first container 100" to distinguish it from the second container 300. The first container 100 is stacked on the second container 300 in such a manner that the lower surface of the flange 102 is in contact with the upper end of the second container 300. In other words, the first container 100 is supported by the upper end of the second container 300. In this way, the liquid culture medium 302 is sandwiched between the back surface 104*b* of the cellulose film 104 and the bottom surface of the second container 300.

Alternatively, after the first container 100 is stacked on the second container 300, the liquid culture medium 302 may be supplied between the back surface 104*b* of the cellulose film 104 and the bottom surface of the second container 300.

Figure 5:
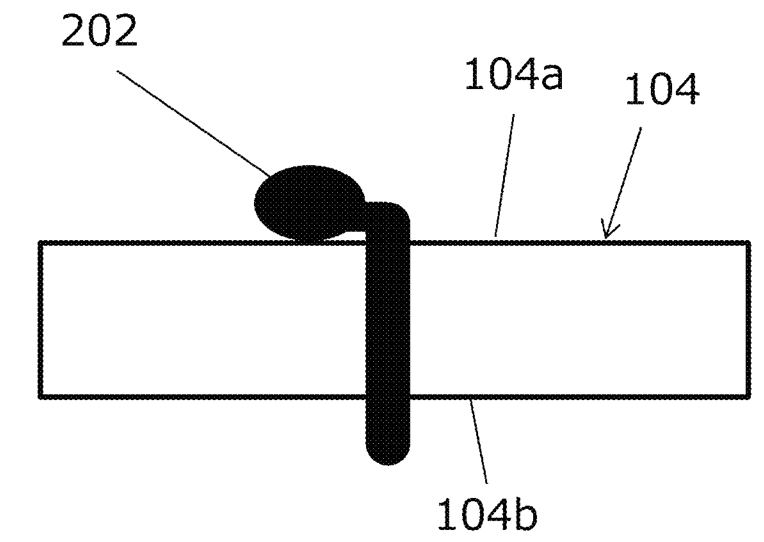
FIG. 5 is a cross-sectional view showing a state where the phytopathogenic fungus has penetrated the cellulose film.

In place of the liquid culture medium 302, a viscous solid culture medium may also be used. As shown in FIG. 6, both of a solid culture medium 304 and the liquid culture medium 302 may be used. In this case, the liquid culture medium 302 is sandwiched between the solid culture medium 304 and the cellulose film 104. As shown in FIG. 5, the incubation of the phytopathogenic fungus 202 which has appeared on the back surface 104*b* is accelerated by at least one of the liquid culture medium 302 and the solid culture medium 304.

(Step (c))

In the step (c), the back surface 104*b* of the cellulose film 104 is observed after the step (b). It is desirable that the back surface 104*b* is observed using an optical microscope.

Only an *Exserohilum* phytopathogenic fungus 202 penetrates the cellulose film 104 to appear on the back surface 104*b* of the cellulose film 104, as described in the step (b). On the other hand, phytopathogenic fungi other than an *Exserohilum* phytopathogenic fungus do not appear on the back surface 104*b* of the cellulose film 104. In this way, in the present invention, only the *Exserohilum* phytopathogenic fungus 202 appears on the back surface 104*b* of the cellulose film 104 selectively.

In the step (c), it is observed whether or not the phytopathogenic fungus 202 appears on the back surface 104*b* of the cellulose film 104.

In particular, whether or not the phytopathogenic fungus 202 appears on the back surface 104*b* of the cellulose film 104 is observed as below.

Figure 8:
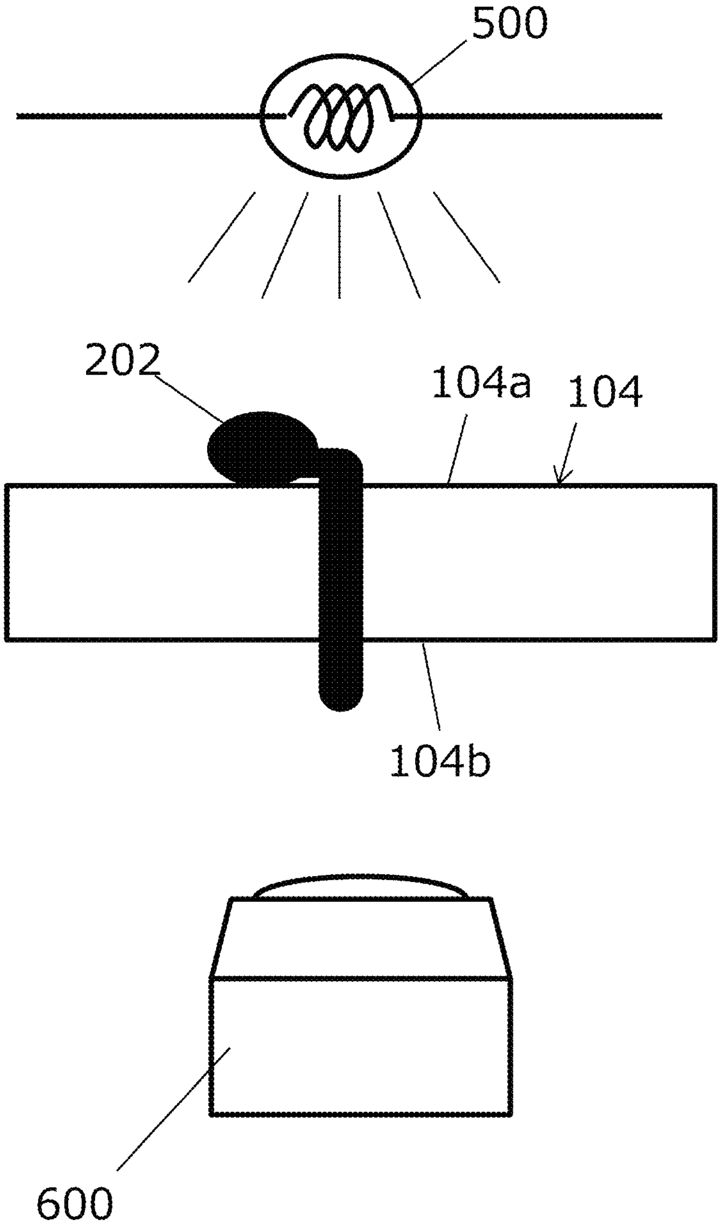
FIG. 8 is a cross-sectional view showing how to observe the fungus from the back surface of the cellulose film.

As shown in FIG. 8, while the cellulose film 104 is irradiated with light emitted from a light source 500 arranged above the front surface 104*a* of the cellulose film 104, the phytopathogenic fungus 202 is observed optically using a microscope 600 arranged below the back surface 104*b* of the cellulose film 104.

Figure 7:
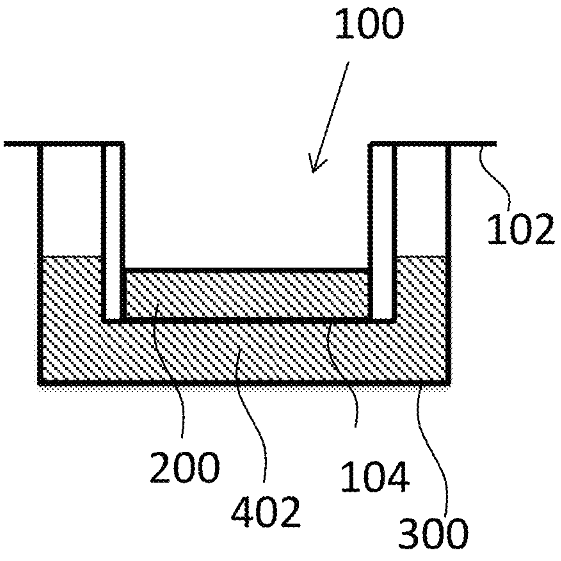
FIG. 7 shows a cross-sectional view, subsequently to FIG. 6, of one example of a method for accelerating the incubation of the fungus.

The liquid culture medium 302 and the solid culture medium 304 are removed from the second container 300. Then, a fluorescent agent having fungus combining ability is added to the inside of the second container 300. Hereinafter, such a fluorescent agent is referred to as "fungus fluorescent agent". The reference number of the fungus fluorescent agent is 402. Then, as shown in FIG. 7, the first container 100 is stacked on the second container 300 having the fungus fluorescent agent 402 therein. Alternatively, the fungus fluorescent agent 402 may be supplied between the back surface 104*b* of the cellulose film 104 and the bottom surface of the second container 300 after the first container 100 is stacked on the second container 300.

A part of the phytopathogenic fungus 202 which has appeared on the back surface 104*b* of the cellulose film 104 is dyed with the fungus fluorescent agent 402. Since the first container 100 is separated from the second container 300 by the cellulose film 104, the fungus fluorescent agent 402 does not spread into the first container 100. For this reason, the non-phytopathogenic fungus contained in the first container 100 is not dyed with the fungus fluorescent agent 402.

Figure 9:
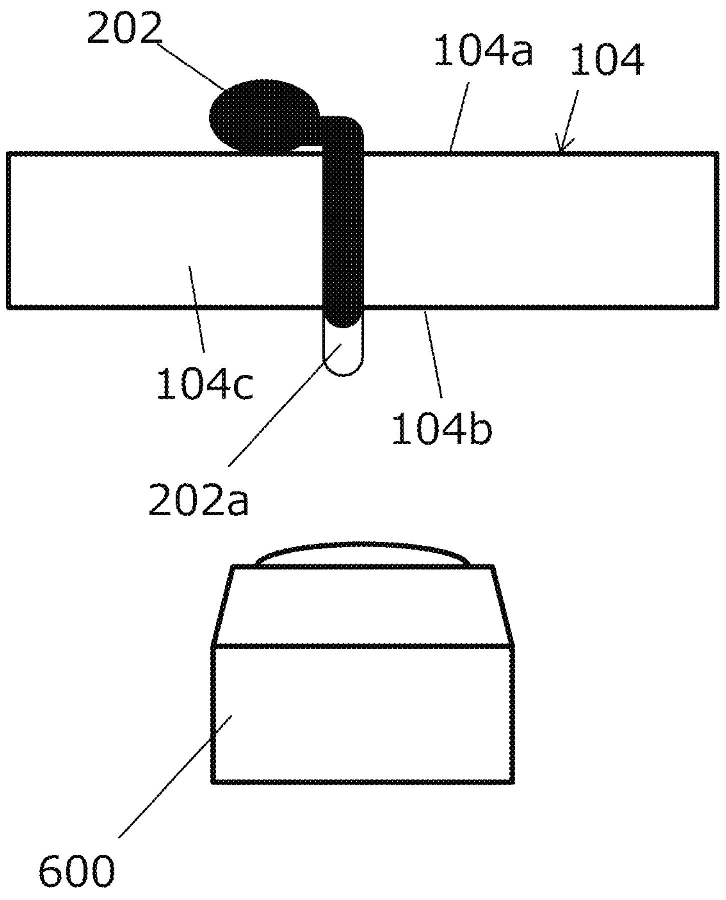
FIG. 9 is a cross-sectional view showing how to observe the fungus from the back surface of the cellulose film.

As shown in FIG. 9, the phytopathogenic fungus 202 dyed with the fungus fluorescent agent 402 is observed using the epifluorescence microscope 600 located under the back surface 104*b* of the cellulose film 104. Needless to say, the phytopathogenic fungus 202 may be observed without using the fungus fluorescent agent 402.

(Step (d))

In the step (d), it is determined that the test sample contains an *Exserohilum* phytopathogenic fungus, if a fungus is found on the back surface 104*b* of the cellulose film 104 in the step (c). Needless to say, it is determined that the test sample does not contain an *Exserohilum* phytopathogenic fungus, if a fungus is not found on the back surface 104*b* of the cellulose film 104 in the step (c).

EXAMPLES

The present invention will be described in more detail with reference to the following examples.

(Incubation of *Exserohium Turcicum*)

*Exserohium turcicum*, one of phytopathogenic fungi, was inoculated on a V-8 agar culture medium. Then, the culture medium was left at rest at a temperature of 25 degrees Celsius for one week. *Exserohium turcicum* was given by a Professor, Dr. Shim, who belongs to Department of Plant Pathology and Microbiology, Texas A&M University.

Then, a part including ends of hyphae was cut together with the culture medium at a size of 1 centimeter×1 centimeter. The cut part was immersed in pure water disposed on a 12-well plate. Each of the pure water has a volume of 1 milliliter.

The water contained in the 12-well plate was observed using an optical microscope. As a result, the present inventors confirmed that spores of *Exserohium turcicum* were released in the water disposed on the 12-well plate. In this way, an aqueous solution containing *Exserohium turcicum* was provided. Hereinafter, this aqueous solution is referred to as "phytopathogenic fungus aqueous solution".

(Preparation of Culture Medium)

The present inventors added the following four reagents to a lactose casein hydrolysate agar medium in accordance with the disclosure of NPL2 to prepare a liquid culture medium 302.

| | |
|---|---|
| Carbendazim | 60 milligrams/liter |
| Captan | 30 milligrams/liter |
| Streptomycin sulfate | 600 milligrams/liter |
| Neomycin sulfate | 300 milligrams/liter |

The thus-prepared liquid culture medium 302 was supplied into the second container 300.

(Experiment 1)

The experiment 1 is composed of inventive examples 1A-1G.

Inventive Example 1A

The first container 100 shown in FIG. 1 was prepared as below.

First, cellulose (available from SIGMA-ALDRICH Co. LLC, trade name: Avicel PH-101) was dissolved in an ionic liquid to prepare a cellulose solution having a concentration of 7%. The ionic liquid was 1-butyl-3-methyl imidazolium chloride (available from SIGMA-ALDRICH Co. LLC).

The cellulose solution was warmed to 60 degrees Celsius. Then, the cellulose solution was applied by a spin coat method for thirty seconds at a rotation speed of 2,000 rpm onto a back surface of a container having a polyethylene terephthalate film on the bottom surface thereof (available from Merck KGaA, trade name: Millicell PIEP 12R 48). The polyethylene terephthalate film served as the substrate 170. The polyethylene terephthalate film randomly had a plurality of through holes 172. In this way, the cellulose film 104 having a thickness of 14.5 micrometers was formed on the back surface of the polyethylene terephthalate film.

The container was left at rest in ethanol at room temperature for 12 hours. In this way, 1-butyl-3-methyl imidazolium chloride was replaced with ethanol. In other words, 1-butyl-3-methyl imidazolium chloride was removed from the cellulose film 104.

Finally, the container was dried in a vacuum desiccator. In this way, the first container 100 shown in FIG. 1 was obtained. In FIG. 1, note that the polyethylene terephthalate film serving as the substrate 170 is not illustrated.

Then, as shown in FIG. 6, the first container 100 was stacked on the second container 300. The back surface **104*b* of the cellulose film 104 was in contact with the liquid culture medium 302. Subsequently, water having a volume of 200 microliters was added to the inside of the first container 100**. Furthermore, the phytopathogenic fungus aqueous solution containing 1,000 spores of *Exserohium turcicum* was added to the inside of the first container 100.

The first container 100 was left at rest at a temperature of 30 degrees Celsius for 24 hours. In other words, in the inventive example 1A, the incubation time was 24 hours.

Figure 10:
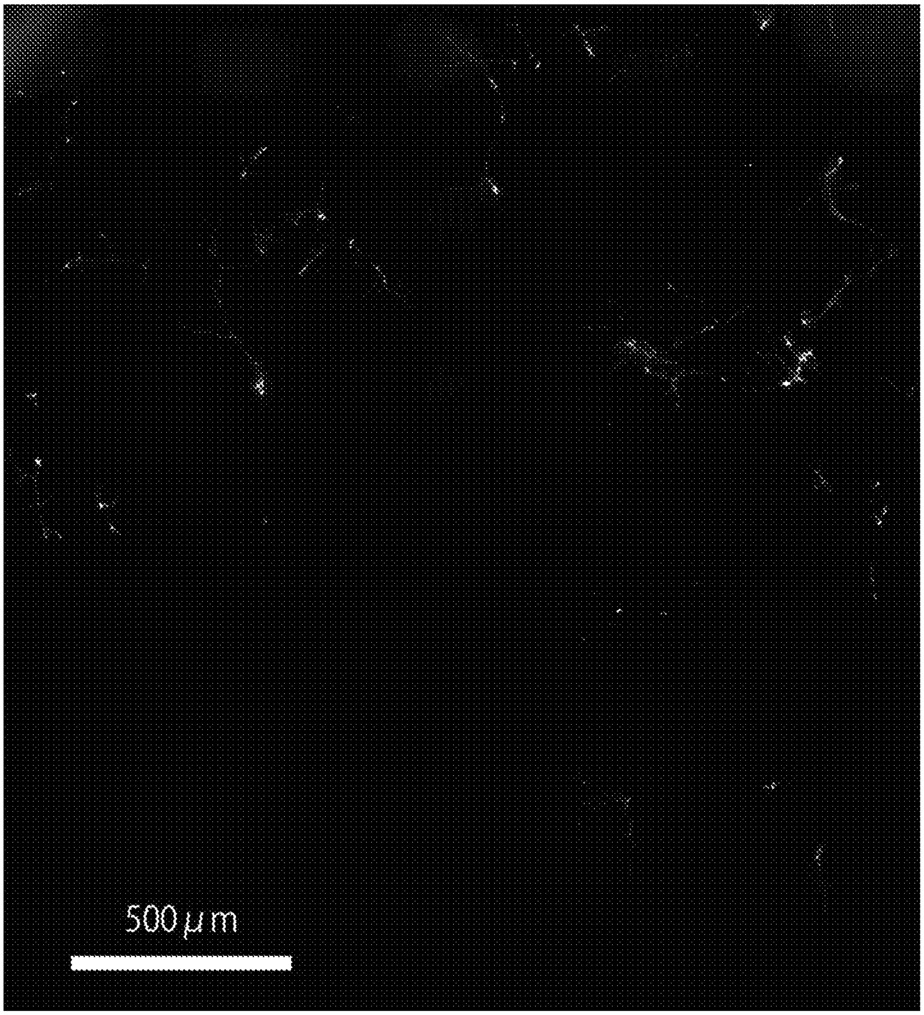
FIG. 10 is a microscope photograph of the back surface of the cellulose film in the inventive example 1A.
Figure 11:
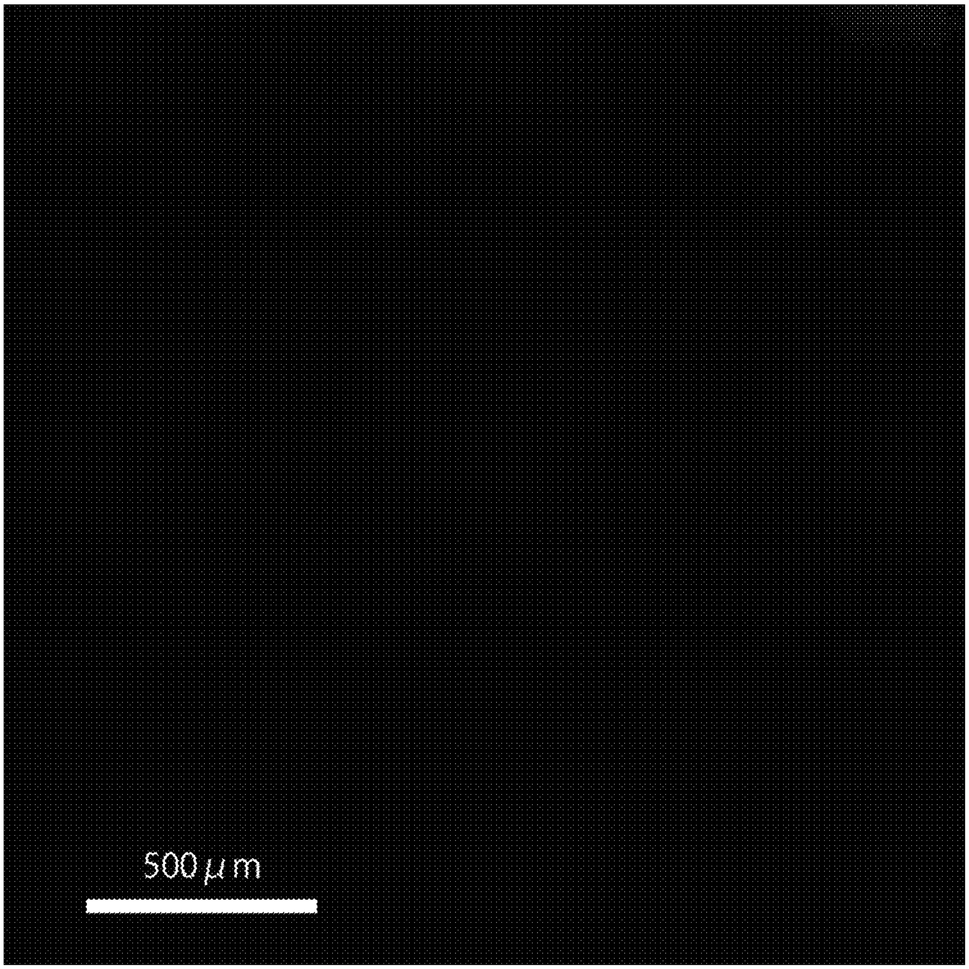
FIG. 11 is a microscope photograph of the back surface of the cellulose film in the comparative example 2A.
Figure 12:
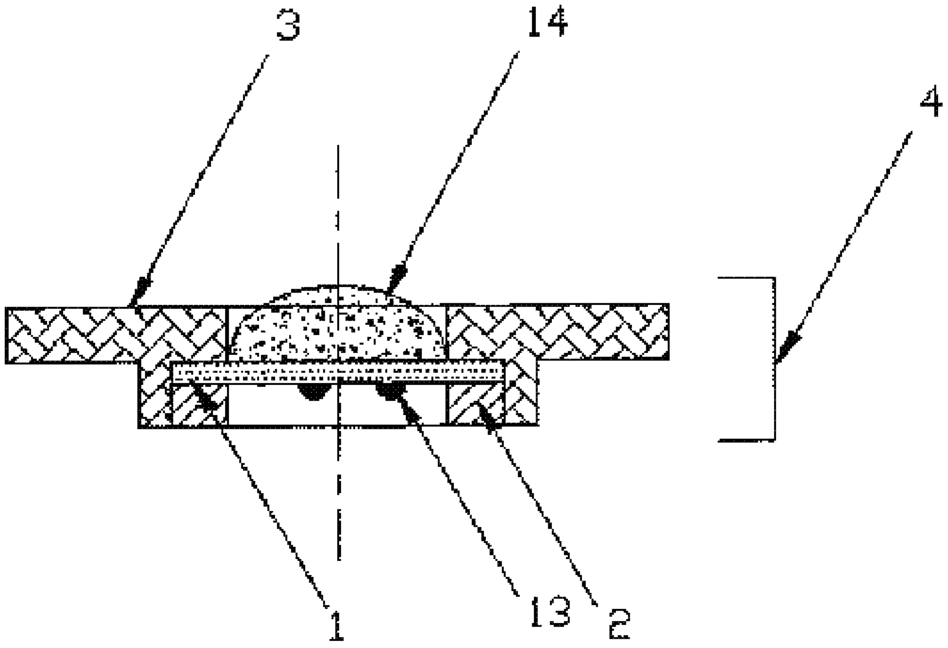
FIG. 12 shows a cross-sectional view of the microporous membrane supporting material used for the method for counting the number of mold cells disclosed in PTL1.

The number of the hyphae of *Exserohium turcicum* which appeared on the back surface **104*b* of the cellulose film 104** was counted visually with an optical microscope. The inventive example 1A was repeated fifteen times. As a result, the mean value of the number of the hyphae of *Exserohium turcicum* which appeared on the back surface **104*b* was 35.5. FIG. 10 is a microscope photograph of the back surface 104*b* of the cellulose film 104** in the inventive example 1A.

(Experiment 2)

In the experiment 2, an experiment similar to the experiment 1 was conducted, except for using *Gibberella fujikuroi* in place of *Exserohium turcicum*. The experiment 2 is composed of comparative examples 2A-2G. Similarly to the *Exserohium turcicum, Gibberella fujikuroi* is one of phytopathogenic fungi.

(Experiment 3)

In the experiment 3, an experiment similar to the experiment 1 was conducted, except for using *Fusarium avenaceum* in place of *Exserohium turcicum*. The experiment 3 is composed of comparative examples 3A-3G. Similarly to the *Exserohium turcicum, Fusarium avenaceum* is one of phytopathogenic fungi.

(Experiment 4)

In the experiment 4, an experiment similar to the experiment 1 was conducted, except for using *Glomerella tucumanensis* in place of *Exserohium turcicum*. The experiment 4 is composed of comparative examples 4A-4G. Similarly to the *Exserohium turcicum, Glomerella tucumanensis* is one of phytopathogenic fungi.

The following Table 1-Table 4 show the number of the hyphae which penetrated the cellulose film 104 in the experiment 1-the experiment 4.

TABLE 1

| | Film thickness (μm) | Name of Fungus | Number of hyphae which penetrated cellulose film 104 |
|---|---|---|---|
| I. example 1A | 14.5 | *Exserohium turcicum* | 35.5 |
| I. example 1B | 5.7 | (phytopathogenic) | 59 |
| I. example 1C | 3.7 | | 149 |
| I. example 1D | 2.0 | | 198 |
| I. example 1E | 0.5 | | 399 |

TABLE 1-continued

| | Film thickness (μm) | Name of Fungus | Number of hyphae which penetrated cellulose film 104 |
|---|---|---|---|
| I. example 1F | 0.2 | | 202 |
| I. example 1G | 0.04 | | 219 |

Incubation time: 24 hours
I.: Inventive

TABLE 2

| | Film thickness (μm) | Name of Fungus | Number of hyphae which penetrated cellulose film 104 |
|---|---|---|---|
| C. example 2A | 14.5 | *Gibberella fujikuroi* | 0 |
| C. example 2B | 5.7 | (phytopathogenic) | 0 |
| C. example 2C | 3.7 | | 0 |
| C. example 2D | 2.0 | | 0 |
| C. example 2E | 0.5 | | 0 |
| C. example 2F | 0.2 | | 0 |
| C. example 2G | 0.04 | | 0 |

Incubation time: 24 hours
C.: Comparative

TABLE 3

| | Film thickness (m) | Name of Fungus | Number of hyphae which penetrated cellulose film 104 |
|---|---|---|---|
| C. example 3A | 14.5 | *Fusarium avenaceum* | 0 |
| C. example 3B | 5.7 | (phytopathogenic) | 0 |
| C. example 3C | 3.7 | | 0 |
| C. example 3D | 2.0 | | 0 |
| C. example 3E | 0.5 | | 0 |
| C. example 3F | 0.2 | | 0 |
| C. example 3G | 0.04 | | 0 |

Incubation time: 24 hours
C.: Comparative

TABLE 4

| | Film thickness (μm) | Name of Fungus | Number of hyphae which penetrated cellulose film 104 |
|---|---|---|---|
| C. example 4A | 14.5 | *Glomerella* | 0 |
| C. example 4B | 5.7 | *tucumanensis* | 0 |
| C. example 4C | 3.7 | (phytopathogenic) | 0 |
| C. example 4D | 2.0 | | 0 |
| C. example 4E | 0.5 | | 0 |
| C. example 4F | 0.2 | | 0 |
| C. example 4G | 0.04 | | 0 |

Incubation time: 24 hours
C.: Comparative

As is clear from Table 1-Table 4, only *Exserohium turcicum* appeared on the back surface **104*b* of the cellulose film 104**. On the other hand, phytopathogenic fungi other than

*Exserohium turcicum* did not appeared on the back surface 104*b* of the cellulose film 104.

INDUSTRIAL APPLICABILITY

The present invention can be used to determine easily whether or not a test sample such as agricultural water or soil contains an *Exserohium* phytopathogenic fungus.

REFERENCE SIGNS LIST

100 First container
 102 Flange
  104 Cellulose film
   104*a* Front surface
   104*b* Back surface
170 Substrate
 170*a* Front surface
 170*b* Back surface
200 Test sample
 202 Phytopathogenic fungus
  202*a* Part of Phytopathogenic fungus
 300 Second container
  302 Liquid culture medium
  304 Solid culture medium
 402 Fluorescent agent having fungus combining ability
 500 Light source
 600 Microscope

The invention claimed is:

1. A method for determining whether or not a test sample contains an *Exserohilum* phytopathogenic fungus, the method comprising:
(a) putting the test sample on a front surface of a cellulose film having no through hole and which forms a portion of a bottom of a container;
(b) incubating the test sample at room temperature for a predetermined time after step (a);
(c) inspecting and quantifying a back surface of the cellulose film outside of the container after step (b) for fungi hyphae; and
(d) identifying the *Exserohilum* phytopathogenic fungus from the test sample if a fungus which has penetrated the cellulose film is found on the back surface of the cellulose film in step (c);
wherein the method further comprises a step of supplying a culture medium to the test sample before step (b); and the culture medium is a lactose casein hydrolysate agar medium containing: carbendazim; captan; streptomycin sulfate; and neomycin sulfate,
wherein the predetermined time is greater than or equal to 24 hours, and wherein the back surface of the cellulose film is an external surface of the container.

2. The method according to claim 1, further comprising:
a step of bringing the back surface of the cellulose film into contact with a fluorescent agent having fungus combining ability between the step (b) and the step (c).

3. The method according to claim 1, wherein
the culture medium is a liquid culture medium.

4. The method according to claim 1, wherein
the culture medium is a solid culture medium.

5. The method according to claim 1, wherein
the cellulose film is supported by a substrate provided on at least one of the front surface and the back surface of the cellulose film; and
the substrate comprises a through hole.

6. The method according to claim 1, wherein
the test sample is solid.

7. The method according to claim 6, wherein
the solid test sample is at least one selected from the group consisting of soil and a crushed plant.

8. The method according to claim 1, wherein
the test sample is liquid.

9. The method according to claim 8, wherein
the liquid test sample is at least one selected from the group consisting of agricultural water, a liquid used for hydroponic culture, a liquid used for washing a plant, a liquid extracted from a plant, a liquid used for washing an agricultural material, and a liquid used for washing clothing or a shoe.

10. The method according to claim 1,
further comprising a step of determining the *Exserohilum* phytopathogenic fungus is *Exserohilum turcicum.*

11. The method according to claim 1, wherein
the cellulose film has a thickness of not less than 0.04 micrometers and not more than 14.5 micrometers.

12. A method for determining whether or not a test sample contains an *Exserohilum* phytopathogenic fungus, the method comprising:
(a) putting the test sample on a front surface of a cellulose film having no through hole and which forms a portion of a bottom of a container;
(b) incubating the test sample at room temperature for a predetermined time after step (a);
(c) inspecting and quantifying a back surface of the cellulose film outside of the container after step (b) for fungi hyphae; and
(d) identifying the *Exserohilum* phytopathogenic fungus from the test sample if a fungus which has penetrated the cellulose film is found on the back surface of the cellulose film in step (c);
wherein in step (b) during the incubation the back surface of the cellulose film is in contact with a culture medium; and the culture medium is a lactose casein hydrolysate agar medium containing: carbendazim; captan; streptomycin sulfate; and neomycin sulfate,
wherein the predetermined time is greater than or equal to 24 hours, and wherein the back surface of the cellulose film is an external surface of the container.

13. The method according to claim 12, further comprising:
a step of bringing the back surface of the cellulose film into contact with a fluorescent agent having fungus combining ability between the step (b) and the step (c).

14. The method according to claim 12, wherein
the culture medium is a liquid culture medium.

15. The method according to claim 12, wherein
the culture medium is a solid culture medium.

16. The method according to claim 12, wherein
the cellulose film is supported by a substrate provided on at least one of the front surface and the back surface of the cellulose film; and
the substrate comprises a through hole.

17. The method according to claim 12, wherein
the test sample is solid.

18. The method according to claim 17, wherein
the solid test sample is at least one selected from the group consisting of soil and a crushed plant.

19. The method according to claim 12, wherein
the test sample is liquid.

20. The method according to claim 19, wherein
the liquid test sample is at least one selected from the group consisting of agricultural water, a liquid used for hydroponic culture, a liquid used for washing a plant, a liquid extracted from a plant, a liquid used for washing an agricultural material, and a liquid used for washing clothing or a shoe.

21. The method according to claim 12, further comprising a step of determining the *Exserohilum* phytopathogenic fungus is *Exserohilum turcicum.*

22. The method according to claim 12, wherein the cellulose film has a thickness of not less than 0.04 micrometers and not more than 14.5 micrometers.

* * * * *